United States Patent [19]

Lohmar et al.

[11] 4,022,826

[45] May 10, 1977

[54] PRODUCTION OF BETA-HALOGENOFORMYL-ETHYL PHOSPHINIC ACID HALIDES

[75] Inventors: Elmar Lohmar, Rodenkirchen; Klaus Gehrmann, Erftstadt-Lechenich; Alexander Ohorodnik, Erftstadt-Liblar; Paul Stutzke, Walberberg, all of Germany

[73] Assignee: Hoechst Aktiengesellschaft, Frankfurt am Main, Germany

[22] Filed: June 29, 1976

[21] Appl. No.: 700,769

[30] Foreign Application Priority Data

July 3, 1975 Germany ............................ 2529731

[52] U.S. Cl. .............................................. 260/543 P
[51] Int. Cl.² ...................... C07F 9/34; C07D 53/22
[58] Field of Search ........ 260/543 P, 543 R, 544 Y

[56] References Cited

FOREIGN PATENTS OR APPLICATIONS 173,763  8/1965  U.S.S.R. ...................... 260/543 P

OTHER PUBLICATIONS

Khairullm et al. I, "Zh. Obs. Chem.," vol. 36, No. 3, pp. 494–498 (1966).
Khairullm et al. II, "Zh. Obs. Chem.," vol. 36, No. 2, pp. 296–302 (1966).
Khairullm et al. III, "Zh. Obs. Chem.," vol. 36, No. 2, pp. 289–296 (1966).
Khairullm et al. IV, "Zh. Obs. Chem.," vol. 38, No. 2, pp. 288–292 (1968).
Khairullm et al. V, "Zh. Obs. Chem.," vol. 37, No. 3, pp. 710–714 (1967).

Primary Examiner—Norman Morgenstern
Attorney, Agent, or Firm—Connolly and Hutz

[57] ABSTRACT

Beta-halogenoformyl-ethyl phosphinic acid halides of the general formula:

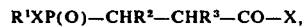

$$R^1XP(O)-CHR^2-CHR^3-CO-X,$$

in which $R^1$ stands for an alkyl radical having 1, 2, 3 or 4 carbon atoms or a phenyl radical, $R^2$ and $R^3$ each stand for hydrogen or $CH_3$, and X stands for chlorine or bromine, are produced by reacting an alkyldihalogenophosphine having 1, 2, 3 or 4 carbon atoms in its alkyl radical, or a phenyldihalogenophosphine, with acrylic acid, methacrylic acid or crotonic acid. To this end, a quantity of the desired beta-halogenoformyl-ethyl phosphinic acid halide is introduced into a reaction zone and circulated in the form of a melt at 50° to 120° C and at a flow rate of 0.1 to 3 m/s., through a heat exchanger; the circulated phosphonic acid halide is admixed with equimolar proportions of the respective starting materials and the resulting mixture is allowed to undergo reaction for a period of 5 to 120 minutes, and beta-halogenoformyl-ethyl phosphinic acid halide is removed.

2 Claims, 1 Drawing Figure

U.S. Patent    May 10, 1977    4,022,826
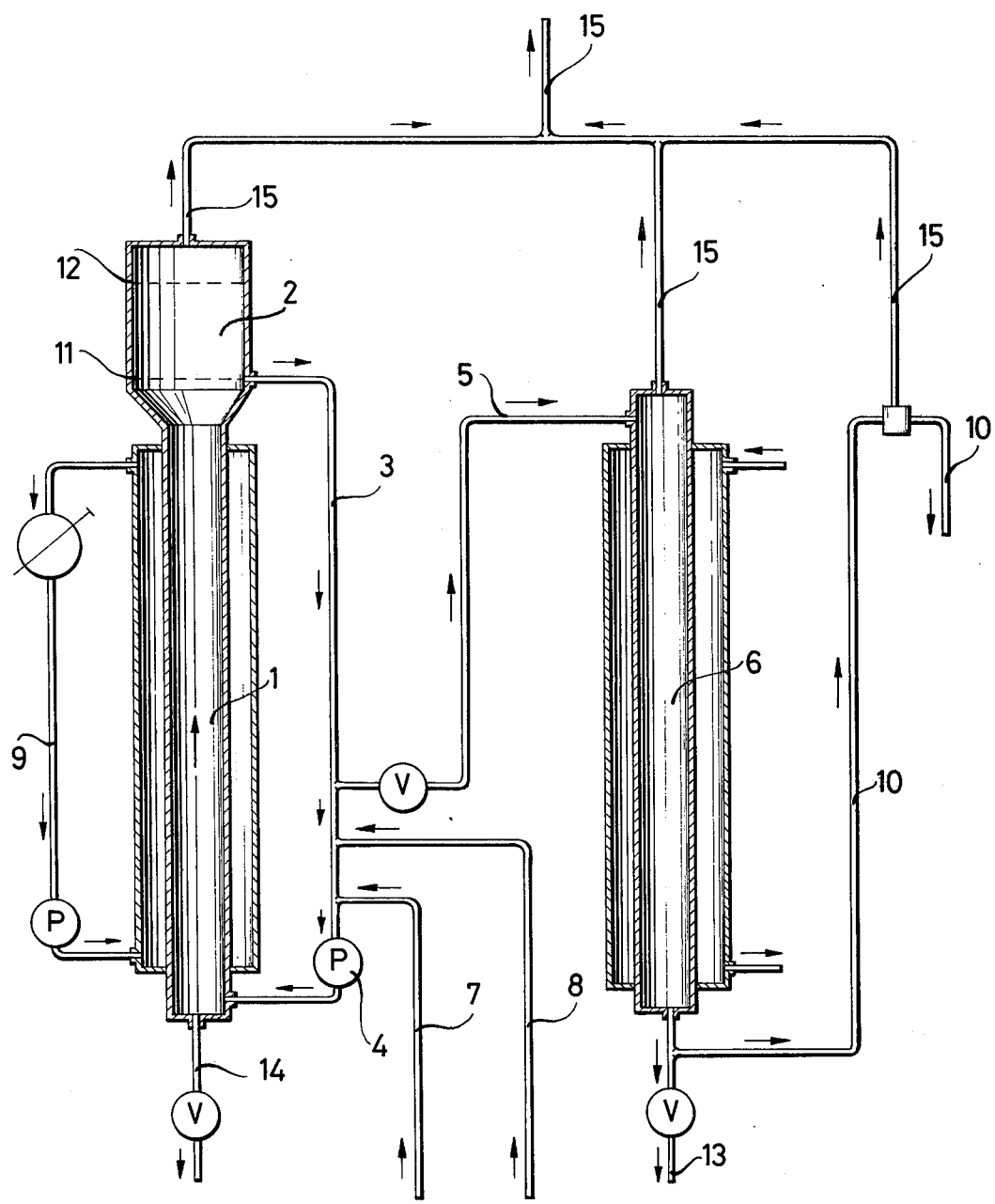

PRODUCTION OF BETA-HALOGENOFORMYL-ETHYL PHOSPHINIC ACID HALIDES

This invention relates to the production of beta-halogenoformyl-ethyl phosphinic acid halides of the general formula: $R^1XP(O)-CHR^2-CHR^3-CO-X$, in which $R^1$ stands for an alkyl radical having 1, 2, 3 or 4 carbon atoms or a phenyl radical, $R^2$ and $R^3$ each stand for hydrogen or $CH_3$, and X stands for chlorine and bromine, by reacting an alkyldihalogenophosphine having 1, 2, 3 or 4 carbon atoms in its alkyl radical, or a phenyldihalogenophosphine, with acrylic acid, methacrylic acid or crotonic acid.

Various processes using this reaction have already been described. Thus, it has been possible to produce beta-chloroformyl-ethyl methyl phosphinic acid chloride in a yield of 72% of the theoretical by reacting methyldichlorophosphine with acrylic acid at temperatures lower than 36° C and distilling the resulting reaction product (Z. Obsc.Chim. 37 (1967), pages 710–714; cf. Example 1 hereinafter). It has also been possible to produce beta-chloroformyl-beta-methyl-ethyl methyl phosphinic acid chloride in a yield of 86% of the theoretical by reacting methyldichlorophosphine with methacrylic acid at temperatures lower than 28° C and distilling the resulting reaction product (Z.Obsc.-Chim. 38 (1968), pages 288–292; cf. Example 3 hereinafter). In a further process, described in USSR Patent Specification No. 173,763, beta-chloroformyl-ethyl phenyl phosphinic acid chloride is produced in a yield as low as 9.5% of the theoretical (cf. Example 2 hereinafter) by reacting phenyldichlorophosphine and acrylic acid in benzene at temperatures of up to 80° C for a period of 13 hours and distilling the resulting reaction product.

USSR Patent Specification No. 173,763 also describes the preparation of beta-chloroformyl-ethyl ethyl phosphinic acid chloride by reacting ethyldichlorophosphine and acrylic acid in benzene at temperatures of up to 60° C, over a period of 2.5 hours, and distilling the reaction product, which is obtained in a yield of 62.4% of the theoretical. In the absence of the benzene solvent, the temperature increases spontaneously to 150° C, and the yield falls to 31.6% of the theoretical. The reaction of ethyldichlorophosphine with methacrylic acid, in the absence of a solvent, produces beta-chloroformyl-beta-methyl-ethyl ethyl phosphinic acid chloride in a yield of 37.2% of the theoretical.

In the reactions just described, the heat evolved is 30–35 kcal per mol of beta-halogenformyl-ethyl phosphinic acid halide. In view of the quantity of heat evolved, it has been necessary heretofore to allow long reaction periods, and to use fairly low temperatures, in an attempt to minimise the decomposition of the reaction products, which are thermally unstable. In spite of these measures, however, it has not been possible to reduce the formation of byproducts to such an extent that the subsequent distillation of the reaction products would become unnecessary. In addition to this, the product yields and the space-time yields obtainable heretofore are must lower than would be desired.

German Published Patent Specification ("Offenlegungschrift") No. 2,346,787 describes a process wherein beta-halogenoformyl-ethyl phosphinic acid halides are boiled with acetic anhydride and cyclized to form 2,5-dioxo-1-oxa-2phospholane. One of the advantageous uses of cyclic anhydrides of the type represented by this compound is their use in the preparation of polyester materials for the production of filaments, fibres, sheets and articles having very good flame-retardant or self-extinguishing properties. However, in order not to impair the properties, e.g. the coloration, of articles rendered flame-retardant by the use of these polyester materials, it is necessary for the beta-halogenformyl-ethyl phosphinic acid halides from which they are derived to have the high purity heretofore obtainable only by an expensive final distillation.

According to the present invention, we provide a process for the production of a beta-halogenoformyl-ethyl phosphinic acid halide of the general formula: $R^1XP(O)-CHR^2-CHR^3-CO-X$, in which $R^1$ stands for an alkyl radical having 1, 2, 3 or 4 carbon atoms or a phenyl radical, $R^2$ and $R^3$ each stand for hydrogen or $CH_3$, and X stands for chlorine or bromine, by reacting an alkyldihalogenophosphine having 1, 2, 3 or 4 carbon atoms in its alkyl radical, or a phenyldihalogenophosphine, with acrylic acid, methacrylic acid or crotonic acid, which process comprises: introducing, into a reaction zone, a quantity of the desired beta-halogenformyl-ethyl phosphinic acid halide; circulating the said phosphinic acid halide in the form of a melt at a temperature of 50° to 120° C, preferably 60° to 90° C, and at a flow rate of 0.1 to 3 m/s., preferably 0.2 to 2 m/s, through a heat exchanger; admixing the circulated phosphinic acid halide with the respective starting materials, the latter being added in substantially equimolar proportions; allowing the resulting mixture to undergo reaction for a period of 5 to 120 minutes, preferably 20 to 60 minutes; and thereafter removing beta-halogenoformyl-ethyl phosphinic acid halide.

A preferred feature of the present invention provides for the process to be carried out continuously by removing material from the reaction zone wherein circulation takes place, and introducing it into a supplementary reaction zone, hereinafter called simply a post-reaction zone, maintained at a temperature of 50° to 120° C, preferably 60° to 90° C, from which post-reaction zone the desired beta-halogenoformyl-ethyl phosphinic acid halide is continuously removed after spending 5 to 120 minutes, preferably 20 to 60 minutes, therein.

The invention will now be described more fully with reference to the accompanying drawings, the single FIGURE of which comprises a diagrammatic representation of an apparatus employed, in a preferred version of the present process, for the production of beta-chloroformyl-ethyl methyl phosphinic acid chloride.

The apparatus represented in the drawing comprises a heat exchanger constituted by a jacketed reactor 1, an expansion vessel 2 disposed above the reactor, a recycle line 3, a circulating pump 4, an overflow line 5, and a jacketed post-reactor 6. The latter may be omitted, however, without the apparatus thereby departing from the scope of the invention.

The reactor 1 is filled up to the level indicated at 11, i.e., to the top of the recycle line 3, with beta-chloroformyl-ethyl methyl phosphinic acid chloride, and heated to a temperature above 60° C, to avoid crystallization. When the reactor has been filled up to the level indicated at 11, the material which it contains is circulated by means of the pump 4 whereby it becomes intimately mixed and is effectively contacted with the heat-dissipating internal surface of the jacketed reactor 1.

Next, acrylic acid is supplied through a line 7 and methyldichlorophosphine (CH$_3$PCl$_2$) is supplied through a line 8, these two reactants being introduced in substantially equimolar proportions. The reaction heat evolved is dissipated via a coolant cycle line 9 which is connected to an inlet and an outlet of the jacket of the reactor 1. The cooling medium (water) is maintained at a temperature above the melting point of beta-chloroformyl-ethyl methyl phosphinic acid chloride (58°–61° C).

In continuous operation, the mixture leaving the reactor 1 through the overflow line 5 is delivered to the jacketed post-reactor 6, in which it is allowed to remain for a period of time substantially equal to that which it spends in the reaction system comprising components 1 to 4, so that it can fully react in the post-reactor, from which it can be removed through an overflow line 10. In the method of operation just described, the overflow line 5 is used with the reactor 1 filled up to the level indicated at 11. The base portion of the post-reactor 6 terminates in a discharge line 13 which is used when the post-reactor has to be cleaned. The expansion vessel 2, the post-reactor 6 and the overflow line 10 are all provided at their respective highest levels with vent pipes as shown at 15.

For discontinuous operation, the procedure is as described for continuous operation, except that the overflow line 5 is closed, so that the material in the expansion vessel 2 can rise from level 11 to level 12. As soon as the material has reached the level 12, the introduction of reactants is stopped, and the reaction mixture is circulated through the system comprising components 1 to 4, at 60° C, for as long as is necessary for it to react completely.

The reactor 1 thus functions additionally as the post-reactor in the case of discontinuous operation. In this case, beta-chloroformyl-ethyl methyl phosphinic acid chloride is removed through line 14. The quantity of material which can be dealt with at one time in batchwise operation depends on the volume provided between level 11 and level 12 in the expansion vessel 2.

The rate of reaction is practically the same in continuous operation as it is in discontinuous operation, inasmuch as heat abstraction is comparable in the two cases, and the material is kept moving during the entire reaction period. This is one respect in which the present process compares favourably with prior art methods using an agitator-containing reaction vessel, for example. As a result of the initially low level of material in an agitator-containing vessel, the cooling surface available at the start of the reaction is very small; the effective cooling surface increases only when the level of the material in the vessel rises. The quantity of heat which is to be dissipated, however, remains constant for a given rate of introduction of the starting materials. In other words, it is necessary either to arrange that the reaction in the agitator-containing vessel shall proceed initially at a very low rate (at the price, however, of a low space-time yield), or, in the event of the starting materials being introduced at a uniform rate, to accept a situation in which it is impossible for the heat evolved at the start of the reaction to be completely dissipated and in which the product may therefore be thermally decomposed. Needless to say, the quality of the product is thereby impaired, so that it has to be subjected to purifying treatment, which is unnecessary in the process of the present invention. The above-mentioned adverse effects have been indicated in USSR Patent Specification No. 173,763, Example 2 of which discloses a spontaneous temperature increase to 150° C, which is coupled with a low yield of only 37% of the theoretical.

The present process thus enables the adverse effects encountered in the prior art methods to be avoided. More particularly it makes it possible, without the use of any solvent, to produce the respective substituted phosphinic acid halides in very satisfactory space-time yields of approximately 3 kg per liter of reactor capacity per hour, and in product yields of up to 99% of the theoretical. The products obtained are sufficiently pure not to need distillative purification before being used as starting materials in making flame-retardant agents, which do have to be very pure.

The following Examples illustrate the invention.

EXAMPLE 1

Preparation of beta-chloroformyl-ethyl methyl phosphinic acid chloride.

The reactor 1 of the apparatus shown in the accompanying drawing was supplied up to the level indicated at 11 with 2 liters of beta-chloroformyl-ethyl methyl phosphinic acid chloride preheated to 60° C. By means of the pump 4, this melt was passed over the heat exchanger surface of the reactor at a velocity of 1 m/s. 2.12 kg/h (29.5 mol) of acrylic acid and 3.45 kg/h (29.5 mol) of methyldichlorophosphine were added simultaneously through the lines 7 and 8, respectively. The reaction heat was dissipated by means of the coolant cycle line 9 to the extent necessary to provide for a constant temperature of 70° C in the reactor 1. The time spent by the material in the reactor 1 was 30 minutes. The material was passed, through overflow line 5, which was heated to 65° C, into the post-reactor 6, which had a capacity of 2 liters and which was also heated to 65° C. After a period of 30 minutes in the post-reactor 6, fully reacted material was removed therefrom in the form of a colourless liquid, through the line 10. 5.56 kg/h of product was removed. The white completely crystalline mass which this product formed on cooling had a melting point of 59° to 61° C. Elementary analysis and $^1$H-NMR-spectroscopy indicated that 99% of the product was beta-chloroformyl-ethyl methyl phosphinic acid chloride. The conversion was quantitative, and the product yield calculated therefrom was 99% of the theoretical. The space-time yield was 2.8 kg of product per liter of reactor capacity per hour. Elementary analysis (wt %): C$_4$H$_7$P Cl$_2$O$_2$ (molecular wt 188.94)

|  | C | H | P | Cl |
|---|---|---|---|---|
| Calculated: | 25.40 | 3.70 | 16.42 | 37.53 |
| Found: | 25.50 | 3.81 | 16.40 | 37.44 |

EXAMPLE 2

Preparation of beta-chloroformyl-ethyl phenyl phosphinic acid chloride.

The apparatus used in Example 1 was supplied with 2 liters of beta-chloroformyl-ethyl phenyl phosphinic acid chloride preheated to 65° C. 1815 g/h (25.2 mol) of acrylic acid and 4.45 kg/h (25 mol) of phenyldichlorophosphine were added through the lines 7 and 8 respectively. The reaction temperature was 70°–72° C and the flow rate of the liquid was 1.8 m/s. The mixture was allowed to remain in the reactor 1 and in the post-reactor 6 for a period of 25 minutes in each case. The conversion was quantitative and 6.25 kg/h of pure beta-chloroformyl-ethyl phenyl phosphinic acid chloride, corresponding to a yield of 99%, was removed. The space-time yield was 3.1 kg of product per liter of reactor capacity per hour. Elementary analysis (wt %): $C_9H_9P Cl_2O_2$ (mol. wt: 250.99)

|  | C | H | P | Cl |
|---|---|---|---|---|
| Calculated: | 43.0 | 3.59 | 12.36 | 28.26 |
| Found: | 43.15 | 3.67 | 12.23 | 28.10 |

EXAMPLE 3

Preparation of beta-chloroformyl-beta-methyl-ethyl methyl phosphinic acid chloride.

The same apparatus was used as in Examples 1 and 2. It was supplied with 2 liters of the above-mentioned acid chloride, preheated to 65° C. Following this 2.58 kg/h (30 mol) of methacrylic acid and 3.51 kg/h (30 mol) of methyldichlorophosphine were added simultaneously. The reaction temperature was 65° C, and the material was circulated at a rate of 0.8 m/s. The mixture was allowed to remain in the reactor 1 and in the post-reactor 6 for 26 minutes in each case. The conversion was quantitative, and 6 kg/h of the above-mentioned acid chloride, corresponding to a yield of 99%, was obtained in pure form. The space-time yield was 3.0 kg of product per liter of reactor capacity per hour. Elementary analysis: $C_5H_9P Cl_2O_2$ (mol. wt: 202.90) (wt %)

|  | C | H | P | Cl |
|---|---|---|---|---|
| Calculated: | 29.57 | 4.44 | 15.27 | 34.95 |
| Found: | 29.41 | 4.61 | 15.11 | 34.75 |

We claim:
1. Process for the production of a beta-halogenoformylethyl phosphinic acid halide of the general formula: $R^1XP(O)$—$CHR^2$—$CHR^3$—$CO$—$X$, in which $R^1$ stands for an alkyl radical having 1, 2, 3 or 4 carbon atoms or a phenyl radical, $R^2$ and $R^3$ each stand for hydrogen or $CH_3$, and X stands for chlorine or bromine, by reacting an alkyldihalogenophosphine having 1, 2, 3 or 4 carbon atoms in its alkyl radical, or a phenyldihalogenophosphine, with acrylic acid, methacrylic acid or crotonic acid, which process comprises: introducing, into a reaction zone, a quantity of the desired beta-halogenoformyl-ethyl phosphinic acid halide; circulating the said phosphinic acid halide in the form of a melt at a temperature of 50° to 120° C and at a flow rate of 0.1 to 3 m/s, through a heat exchanger; admixing the circulated phosphinic acid halide with the respective starting materials, the latter being added in substantially equimolar proportions; allowing the resulting mixture to undergo reaction for a period of 5 to 120 minutes; and thereafter removing beta-halogenformyl-ethyl phosphinic acid halide.

2. The process as claimed in claim 1, which is carried out continuously by removing material from the reaction zone wherein circulation takes place and introducing it into a post-reaction zone, maintained at a temperature of 50° to 120° C, from which post-reaction zone the desired beta-halogenoformyl-ethyl phosphinic acid halide is continuously removed after spending 5 to 120 minutes therein.

* * * * *